United States Patent [19]
Schea, III et al.

[11] Patent Number: 5,181,394
[45] Date of Patent: Jan. 26, 1993

[54] FREEZE PROTECTIVE SHIPPING UNITS

[75] Inventors: Henry E. Schea, III, Oxnard; Kenneth M. Cleary, Jr., Newbury Park, both of Calif.

[73] Assignee: Amgen Inc., Thousand Oaks, Calif.

[21] Appl. No.: 640,603

[22] Filed: Jan. 14, 1991

[51] Int. Cl.⁵ .......................... B65D 81/18; F25D 3/08
[52] U.S. Cl. ........................................ 62/371; 116/219; 62/457.2; 206/570
[58] Field of Search ................ 62/457.2, 457.1, 457.5, 62/457.9, 371; 206/570; 116/219

[56] References Cited

U.S. PATENT DOCUMENTS

| | | | |
|---|---|---|---|
| 3,429,141 | 2/1966 | Halseth | 62/457.1 |
| 4,145,918 | 3/1979 | Couch et al. | 116/219 |
| 4,191,125 | 3/1980 | Johnson | 116/219 |
| 4,250,998 | 2/1981 | Taylor | 62/371 |
| 4,280,336 | 7/1981 | Taylor | 62/457.5 |
| 4,573,581 | 3/1986 | Galloway et al. | 62/457.9 |
| 4,738,364 | 4/1988 | Yeager | 62/457.2 |
| 4,850,484 | 7/1989 | Denman | 62/371 |
| 4,989,419 | 2/1991 | Brando et al. | 62/457.2 |

*Primary Examiner*—Albert J. Makay
*Assistant Examiner*—William C. Doerrler
*Attorney, Agent, or Firm*—Marshall, O'Toole, Gerstein, Murray & Bicknell

[57] ABSTRACT

Disclosed are shipping and/or storage units for containers of liquid compositions, such as solutions of biologically active proteins, which are susceptible to physicochemical change upon freezing. Preferred container holders have double sidewalls and a freeze indicator adjacent a container-accommodating cavity. A phase change material such as a carboxymethylcellulose gel is disposed in the enclosed space between sidewalls and freezes at a temperature higher than the nucleation temperature of the composition. A freeze indicator provides an irreversible visual signal upon reaching a temperature intermediate the nucleation temperature of the liquid composition and the freezing temperature of the phase change material.

12 Claims, 2 Drawing Sheets

FREEZE PROTECTIVE SHIPPING UNITS

BACKGROUND

The present invention relates generally to shipping and/or storage of thermally sensitive materials and more particularly to freeze protective units suitable for use in the transport and storage of products such as those biologically active proteins which may be susceptible to irreversible physicochemical alteration upon freezing.

The art is rich in proposal for the development of insulated storage and transport containers adapted to protect various thermosensitive products such as foodstuffs, medicaments, acrylic paints and the like from damage. While a major focus of such developments has been the protection of thermosensitive products from the adverse effects of elevated temperatures (see, e.g., U.S. Pat. No. 4,903,493), devices have also been developed which function to inhibit product freezing and still other shipping and storage units have been devised for the purpose of insulating products from exposure to both high and low temperature extremes. U.S. Pat. No. 4,738,364, for example, proposes to address the problems associated with safeguarding medicines from reaching either high or low temperature thresholds. Despite the continuous development of increasingly efficient insulating containers for shipment of thermosensitive products, the costs of highly efficient thermal protection are most often balanced against the statistical likelihood of exposure to temperature extremes. The result is that such products are transported and stored in a manner providing protection for most, but certainly not all product shipments. Where the adverse effects of product exposure to temperature extremes are manifest, this presents little risk to the ultimate consumer. Where such effects cannot be readily ascertained, as is frequently the case with medicaments, the risks associated with consumer use of thermally damaged products are significantly increased.

With the recent development of recombinant DNA technologies, increasing numbers of biologically active materials such as peptides, proteins and glycoproteins have become available for research and therapeutic use. Because these products have a significant potency even when administered in minute quantities, they are frequently supplied as dilute aqueous solutions of the active ingredient combined with small quantities of pharmaceutically acceptable adjuvant and carrier substances such as serum albumin. Studies of the effects of temperature extremes on these compositions have surprisingly revealed that freezing can generate physicochemical alterations which are not spontaneously reversible upon thawing. More specifically, the freezing of dilute solutions of biologically active human proteins has been seen to give rise to the formation of both lower and higher molecular weight species of the proteins. These observations have expectedly prompted concern regarding the maintenance of biological potency of the products which have been subjected to freezing. They have also generated significant concerns in an immunological context. To the extent that the observed formation of higher molecular weight species of proteins is reflective of the formation of aggregates of either the projected therapeutic protein with other protein molecules or with non-protein components of the formulation, there is a potential risk that the recipient may develop adverse immunological responses. Such potential risks are, of course, exacerbated by the fact that visual inspection of, e.g., a unit dosage vial containing a solution of a therapeutic protein is insufficient to reveal that the product has undergone freezing at some time during its transport or storage and may therefore contain undesired protein fragments or aggregates.

Consistent with the above, there can be seen to exist a need in the art for new freeze protective packaging units useful in the transport and storage of biologically active products such as those protein solutions which can be susceptible to visually occult physicochemical alteration upon freezing. Ideally, such packaging would allow for the protected transport of therapeutic proteins in the unit dosage glass vials ordinarily employed as containers for therapeutic agents. Desirably, such packaging would facilitate transport in a refrigerated, but not frozen, state and would insulate the contents of the vials against freezing when exposed to extreme cold temperatures such as might occasionally be encountered in the projected distribution environment. The packaging should be cost effective to the extent that it would allow freeze protection in most ordinary transport and storage circumstances. When extraordinarily cold temperatures are nonetheless encountered, the freeze protective packaging would ideally provide means for an after-the-fact determination that the containers have been exposed to the extreme conditions which might cause irreversible physicochemical alteration.

SUMMARY

According to the present invention, novel freeze protective transport and storage units are provided which both insulate containers of liquids from exposure to freezing temperatures and provide for a visual signal indicating that the cold insulative capacity of the devices has been exceeded and the liquids in the containers have been placed at risk of freezing. In preferred embodiments, container holders are provided which are readily and inexpensively thermoformed of plastic materials. The container holders have inner and outer sidewalls. The double walled construction allows container-accommodating cavities to be formed in the inner sidewall and also allows for the development of an enclosed space between the walls and adjacent the cavities. A phase change material is disposed in the enclosed space and operates to insulate liquid filled containers accommodated in the cavities against freezing. Transport and shipment units are also provided with a freeze indicator which signals that liquids in the containers have encountered temperatures at least approaching those at which the contained liquids may freeze Presently preferred units according to the invention include a freeze protective phase change material such as a carboxymethylcellulose gel whose composition is predetermined in a manner allowing its freezing temperature (or temperature range) to be reached upon exposure to temperatures higher than the nucleation temperature of liquid within the containers. The included freeze indicator device is similarly selected so that a signal is provided when it is exposed to a temperature which is no lower than (and preferably higher than) the nucleation temperature of the contained liquid but which is also lower than the freezing temperature of the phase change material In use for the transport and storage of, e.g., therapeutic doses of recombinant-produced human granulocyte colony stimulating factor, the container holder has one or more cavities or wells into which unit dose glass vials are disposed When so disposed, the glass vials are protected from external forces and from lateral movement into contact with other similarly disposed vials. The typical nucleation temperature (i.e., ice nucleating temperature) of aqueous therapeutic solutions of this protein is less than $-10°$ C. and the phase change gel material enclosed between the sidewalls (external to the cavities or wells) is formulated such that its freezing temperature is about $-1°$ C. The freeze indicator provided in the unit would typically be disposed in a cavity or well adjacent to the cavity where vials are inserted and the indicator would be so fashioned as to provide an irreversible signal when it is exposed to a temperature which lower than $-1°$ C. but equal to or higher than $-10°$ C. Suitable freeze indicators include those comprising a liquid dyestuff in a frangible container. A lid is optionally provided to enclose the space where the containers and freeze indicator are positioned. When the unit encounters exposure to the cold, the phase change material insulates the liquid protein composition up to the point where the phase change material itself freezes and can no longer insulate. If the temperature in the unit continues to drop, the freeze indicator is "activated" to provide a signal that the ice nucleating temperature of the aqueous therapeutic composition in the vials has been approached, if not surpassed. This predetermined sequence of events allows the dispenser or ultimate consumer of the therapeutic solution to make an informed decision concerning use of the product.

Numerous aspects and advantages of the invention will be apparent upon consideration of the following detailed description of preferred embodiments thereof, reference being made to the drawing wherein FIG. 1 is a perspective view of a transport and/or storage unit according to the invention showing the typical positioning of vials and freeze indicator;

DETAILED DESCRIPTION

Figure 1:
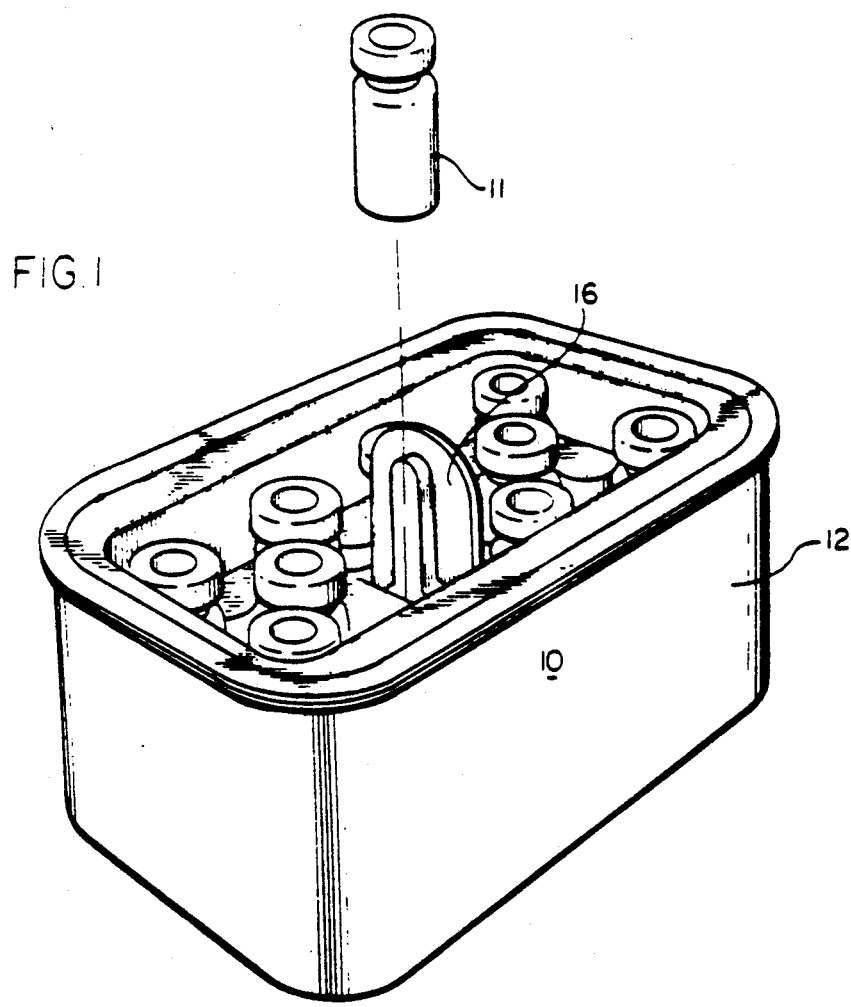
Figure 2:
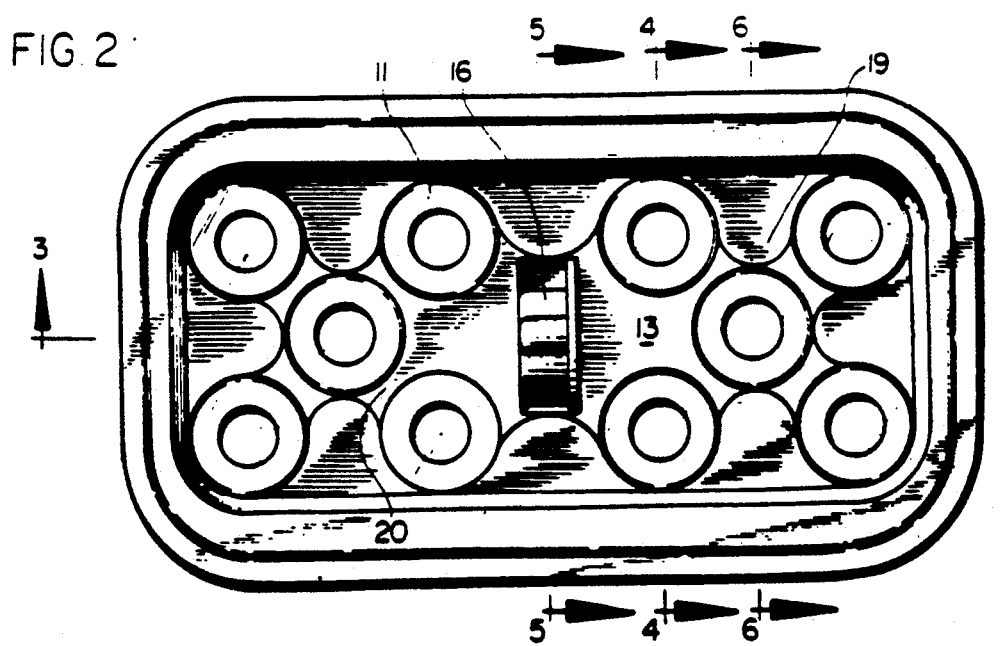
FIG. 2 is a top plan view of a unit as illustrated in FIG. 1.
Figure 3:
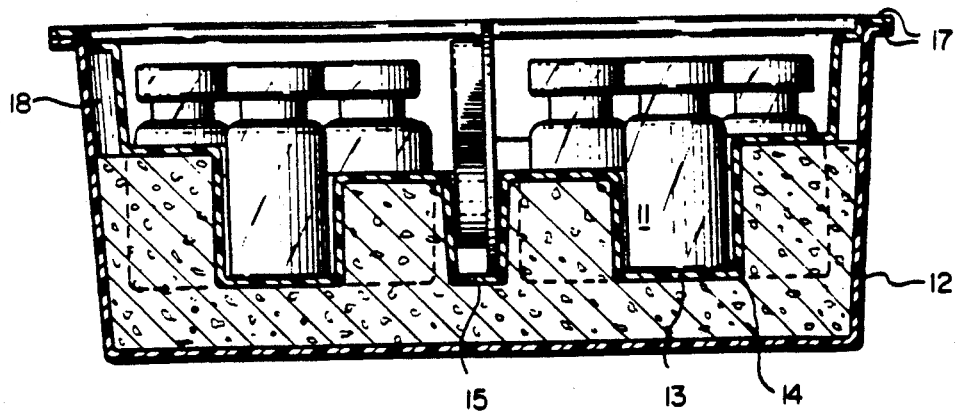
FIG. 3 is a sectional view taken along line 3—3 of FIG. 2.
Figure 4:
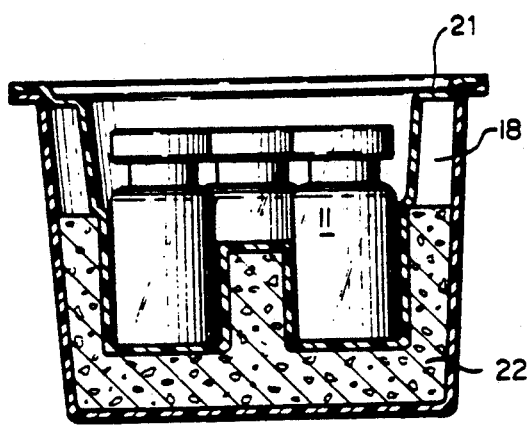
FIG. 4 is a sectional view taken along line 4—4 of FIG. 2.
Figure 5:
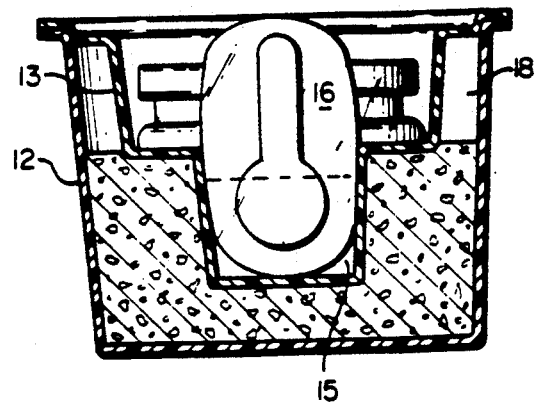
FIG. 5 is a sectional view taken along line 5—5 of FIG. 2.
Figure 6:
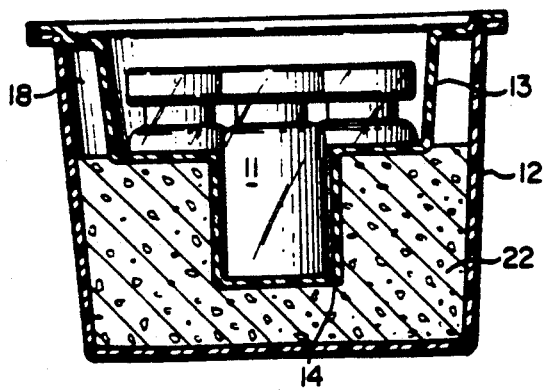
FIG. 6 is a sectional view taken along line 6—6 of FIG. 2.

The present invention specifically addresses problems in the technology associated with the shipment and storage of products which are susceptible to damage upon freezing and more particularly problems encountered in the shipment of liquid compositions which can undergo physicochemical alteration when frozen. Typical compositions of this type include dilute aqueous solutions of proteins such as biologically active proteins intended for scientific research and therapeutic uses. Such substances are commonly supplied in small volume (e.g., 2–3 c.c.) glass vials. The aqueous solutions of proteins commonly include diluents, adjuvants, carriers and a variety of chemical compositions. In certain instances the active ingredient has been noted to undergo physicochemical alteration upon the occurrence of freezing of the aqueous solutions. The alterations are characterized by the presence of higher and lower molecular weight species of the proteins as revealed by chromatographic analysis. These species have not been seen to revert to the original protein species upon warming.

Shipping units according to the invention are designed to protect containers such as glass vials from external forces during transport and correspondingly include one or more cavities or wells into which the cylindrical glass vials may be disposed. The shipping container holders also operate to insulate the vials from the adverse effects of exposure to cold temperatures and for this purpose the container holders are manufactured to provide a double walled conformation with the peripheries of the walls joined to provide an enclosed space around the cavities in which vials are placed. The containers are readily fabricated from thermoplastic materials such as high impact polystyrene, glycol modified polyethylene teraphthalate, and preferably polyvinyl chloride. Typically, the outer wall takes the shape of a rectangular open tray and the inner sidewall has a number of wells to accommodate a number of vials. The outer and inner sidewalls are so dimensioned and shaped that the inner sidewall component can be nested within the outer tray and the upper edges can be solvent or heat sealed together, providing an enclosed space (external to the inner sidewall and internal to the outer sidewall) which surrounds at least part of each cavity or well.

Within the enclosed space between sidewalls, container holders of the invention have a phase change material which, in the most highly preferred embodiments, has a high heat of fusion. While water can serve as the phase change material, the potential for leakage can be problematic so gelled materials such starch gels, agarose gels, gelatin, and especially aqueous carboxymethylcellulose gels are presently preferred. Such gels are also preferred because they have a lesser risk of leakage and provide structural integrity to the units.

The container holders have disposed in them a freeze indicator which will provide visual signal upon exposure to a preselected temperature. Typically, the freeze indicator is positioned adjacent the containers or vials being shipped (i.e., internal to the inner sidewall) and to this end a separate well or cavity may be provided to accommodate the freeze indicator. A lid may be provided to enclose the internal space of the inner sidewall and prevent the vials and freeze indicator from falling out if the holder is tilted or inverted. If desired, the lid may be double walled and may be provided with an insulating phase change material between walls.

The freeze indicator may have a variety of conformations and its only operational constraint is that it provide an irreversible visual signal indicative that a particular low temperature has been reached in the space where the vials are disposed. Thus, while thermocouple devices of varying kinds may be employed, simple devices such as the freeze indicators described in U.S. Pat. No. 4,191,125 are quite suitable. Briefly described these devices include a frangible ampoule of a solution which freezes at a predetermined temperature, causing the ampoule to rupture. The solution, upon warming, is wicked out onto an absorbent paper to provide an easily visible signal.

FIGS. 1–7 illustrate a presently preferred embodiment of a transport and/or storage unit according to the invention wherein container holder 10 is adapted for use in storage of ten cylindrical glass vials 11. Container holder 10 is seen to be constructed from an outer sidewall element 12 and inner sidewall element 13. Outer sidewall 12 has the shape of an open rectangular tray. Inner sidewall 13 is formed with ten cylindrical cavities or wells 14 dimensioned to accommodate disposition of vials 11. In the embodiment illustrated, inner sidewall 13 also includes a centrally disposed rectangular well 15 which accommodates disposition of freeze indicator 16 at a location adjacent wells 14 and vials 11 disposed therein Each of the sidewalls is provided with an outwardly extending lip or flange 17 dimensioned to allow the nesting of inner sidewall 13 in outer sidewall 12. Flanges 17 may be solvent or heat sealed together so that a space 18 is enclosed between the sidewalls and around (external to) the wells formed in inner sidewall 13.

In the embodiment illustrated, vial-accommodating wells 14 are positioned in an array allowing easy insertion and removal of vials. More particularly, the wells are formed with an elevated outer shoulder 19 and a (relatively) depressed inner shoulder 20 allowing space for easy grasp of vials. A lid (not illustrated) may be provided and may rest on step flange 21 to enclose the space surrounding the vials.

Space 18 between sidewalls 12 and 13 is filled at least partially with phase change material 22. A quantity of phase change material is employed such that the space external to wells 14 is filled with the material and a "head space" may be provided, e.g., at either the bottom or top of the container to allow for expansion in the volume of the material upon freezing. To provide head space at the bottom of the container, a cross-linkable liquid gel material is disposed in and partially fills outer sidewall 12, inner sidewall 13 is then nested in the outer sidewall. The two sidewalls are sealed together and the unit is inverted allowing a head space to be formed at the bottom of the unit when the gel solidifies.

Freeze indicator 16 illustrated in this embodiment includes a frangible ampoule filled with a colored aqueous material. The ampoule is surrounded by an absorbent material (such as filter paper) and supported between a rigid backing member and a rigid transport cover member. When the liquid in the ampoule freezes, the ampoule ruptures and upon return to a higher temperature (e.g., room temperature) the liquid is wicked into the absorbent material providing a color signal.

In devices according to the present invention a particular relationship is maintained between the freezing temperature of the liquid transported, the freezing temperature of the phase change material and the temperature at which the freeze indicator will generate a visual signal. More particularly, the freezing temperature of the phase change material is selected to be higher than the nucleation temperature of the liquid material to be transported. The temperature at which the freeze indicator generates its signal is correspondingly selected to be lower than the freezing temperature of the phase change material and equal to or higher than the nucleation temperature of the liquid to be transported.

The following is a description of a presently preferred embodiment of the invention adapted for use in the transportation and storage of glass vials containing dilute aqueous solutions of recombinant human granulocyte colony stimulating factor which have an ice nucleating temperature of about $-10°$ C to $-16°$ C.

Each container holder is manufactured from white colored virgin polyvinyl chloride sheet stock having a 0.040 ($\pm 10\%$) inch gauge. The container holder inner sidewall is thermoformed to provide ten cylindrical wells to accommodate insertion of ten 2 c.c. sealed glass vials and a rectangular well to accommodate insertion of the freeze indicator device. The rectangular (about 4¾ by 2¾ inch) outer sidewall tray has an overall depth of about 1⅛ inches. The inner sidewall is nested in the outer sidewall and radio frequency sealed to provide an enclosed inner space with an approximately ⅜ inch clearance of the bottom of the wells from the bottom of the tray.

Prior to the nesting and sealing of the outer and inner sidewalls, the outer sidewall tray is filled with about 140 grams a freshly prepared mixture of water and 2 percent by weight self-gelling carboxymethylcellulose. This quantity of gel material leaves about 5-10% of the enclosed volume of the container holder as head space. The self gelling material is formulated by P.P.A. Inc., Minneapolis, Minn. as a variant of their Unigel 18-C product which contains 7.5% by weight methyl paraben. The freezing temperature of the gel is about $-1°$ C.

Figure 7:
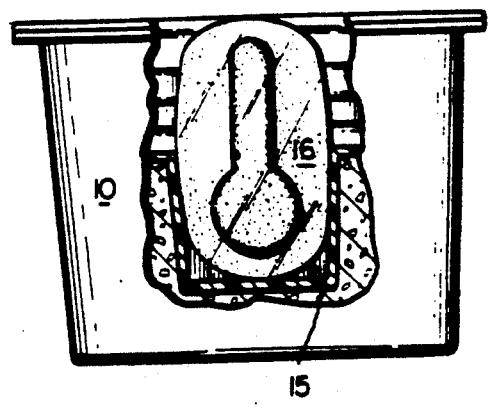
FIG. 7 is a rear elevational view of a unit as illustrated in FIG. 1 with a portion cut away.

The freeze indicator includes a bulb shaped ampoule manufactured by PyMaH Corp., Somerville, N.J., and sold as a component of their FreezeWatch ® part No. 9800 product bearing the notation of U.S. Pat. No. 4,191,125. The ampoule is covered with absorbent filter paper and enclosed in a plastic "blister" packing with a transparent cover. Product specifications call for the ampoule to rupture and release its red colored contents at $-4°$ C. Upon warming thereafter, the red liquid is absorbed by the filter paper providing a clear visual signal (as illustrated in FIG. 7) that a temperature approaching the ice nucleating temperature of the aqueous protein solution has been approached.

Numerous modifications and variations of the invention as disclosed above are expected to occur to those of ordinary skill in the art and consequently only the limitations which appear in the appended claims should be placed thereon.

We claim:

1. A storage unit for containers of a liquid composition susceptible to physicochemical alteration upon freezing, said unit comprising:
   a double-sidewalled container holder including,
   an inner sidewall having formed therein cavity means accommodating the disposition of at least one said container in a position secured against movement,
   an outer sidewall,
   said inner and outer sidewalls of said container holder means defining an enclosed space therebetween and adjacent at least a part of said cavity means;
   a phase change material disposed in and filling at least a portion of said enclosed space adjacent said cavity means, said phase change material having a freezing temperature which is higher than the nucleation temperature of said liquid composition in said container; and,
   a freeze indicator means for generating an irreversible visual signal of the attainment, adjacent said cavity means, of a temperature less than the freezing temperature of said phase change material, but no less than the nucleation temperature of said liquid composition.

2. A storage unit according to claim 1 wherein the visual signal is generated upon attainment of a temperature intermediate the respective nucleation temperature of said liquid composition and the freezing temperature said phase change material.

3. A storage unit according to claim 1 further including a cavity means formed in said inner sidewall and accommodating the disposition therein of said freeze indicator means.

4. A storage unit according to claim 1 including a plurality of spaced apart cavities formed in said inner sidewall and accommodating a plurality of said containers.

5. A storage unit according to claim 1 wherein the visual signal generated by said freeze indicator means is a color signal.

6. A storage unit according to claim 1 wherein said freeze indicator means comprises a frangible ampoule containing a liquid which, upon freezing, expands to rupture said ampoule.

7. A storage unit according to claim 1 wherein said phase change material is an aqueous carboxymethylcellulose gel.

8. A storage unit according to claim 7 wherein said gel fills less than the entire enclosed space between said inner and outer sidewalls.

9. A storage unit according to claim 1 wherein both said inner and outer sidewalls are composed of a thermoformed plastic material.

10. A freeze protective storage unit for a plurality of containers of an aqueous solution of a biologically active protein susceptible to physicochemical alteration upon freezing, said unit comprising:
a double-sidewall container holder including,
an inner sidewall having formed therein a plurality of cavity means accommodating the disposition of a plurality of said containers in a position secured against movement,
an outer sidewall,
said inner and outer sidewalls of said container holder means defining an enclosed space therebetween and adjacent said cavity means;
a phase change material disposed in and filling at least a portion of said enclosed space adjacent said cavity means, said phase change material having a freezing temperature which is higher than the nucleation temperature of the aqueous solution in said containers; and
a freeze indicator means for generating an irreversible visual signal of the attainment, adjacent said cavity means, of a temperature intermediate the freezing temperature of said phase change material and the ice nucleating temperature of said aqueous solution.

11. A storage unit according to claim 10 wherein said inner sidewall includes an additional cavity means accommodating the disposition of said freeze indicator therein in a position secured against movement.

12. A storage unit according to claim 10 wherein the ice nucleating temperature of said aqueous solution is less than $-10°$ C. and the freezing temperature of said phase change material is about $-1°$ C.

* * * * *